United States Patent [19]

Behringer

[11] Patent Number: 4,872,593
[45] Date of Patent: Oct. 10, 1989

[54] DISPENSER FOR PACKAGED BANDAGES AND THE LIKE

[76] Inventor: John W. Behringer, 143 Main St., North Kingstown, R.I. 02852

[21] Appl. No.: 142,832

[22] Filed: Jan. 11, 1988

[51] Int. Cl.⁴ ............................................. B65H 1/08
[52] U.S. Cl. .................................... 221/231; 221/250; 221/259; 221/287; 271/120
[58] Field of Search ................. 221/241–243, 221/231, 258–260, 250, 277, 198, 287; 271/119, 120

[56] References Cited

U.S. PATENT DOCUMENTS

| | | | |
|---|---|---|---|
| 1,131,112 | 3/1915 | Brown | 221/231 |
| 1,466,492 | 8/1923 | Stiriss | 221/241 |
| 2,036,921 | 4/1936 | Christmas | 221/250 |
| 3,151,771 | 10/1964 | Greere | 221/198 |
| 3,220,605 | 11/1965 | Casey | 271/120 |
| 3,294,285 | 12/1966 | Kovacevic | 221/242 |
| 3,649,003 | 3/1972 | Muller et al. | 271/120 |
| 3,887,106 | 6/1975 | Marlin et al. | 221/259 |
| 4,043,549 | 8/1977 | Rinehart | 271/120 |
| 4,084,807 | 4/1978 | Terajima et al. | 271/119 |

FOREIGN PATENT DOCUMENTS 813637  6/1937  France ................................ 221/259

Primary Examiner—H. Grant Skaggs
Attorney, Agent, or Firm—Jones, Day, Reavis & Pogue

[57] ABSTRACT

An apparatus is provided for the storage and dispensing of packaged adhesive bandages and similarly shaped flat packaged units. The dispenser includes a drive unit base, which may be powered either manually or electrically. A cartridge is removably mountable to the top of the base. The cartridge holds a stack of packaged adhesive bandages on a floor in which is defined an elongated slot. A weight is provided to exert downward pressure against the bandages toward the cartridge floor. A roller with an elastic following finger attached to the roller is mounted within the housing and aligned with the slot in the floor. When the roller is rotated the following finger frictionally engages the lowermost bandage in the stack, urging it through an exit portal at one end of the cartridge. As the bandage is propelled through the portal, it displaces a resilient flap which covers the portal.

11 Claims, 3 Drawing Sheets

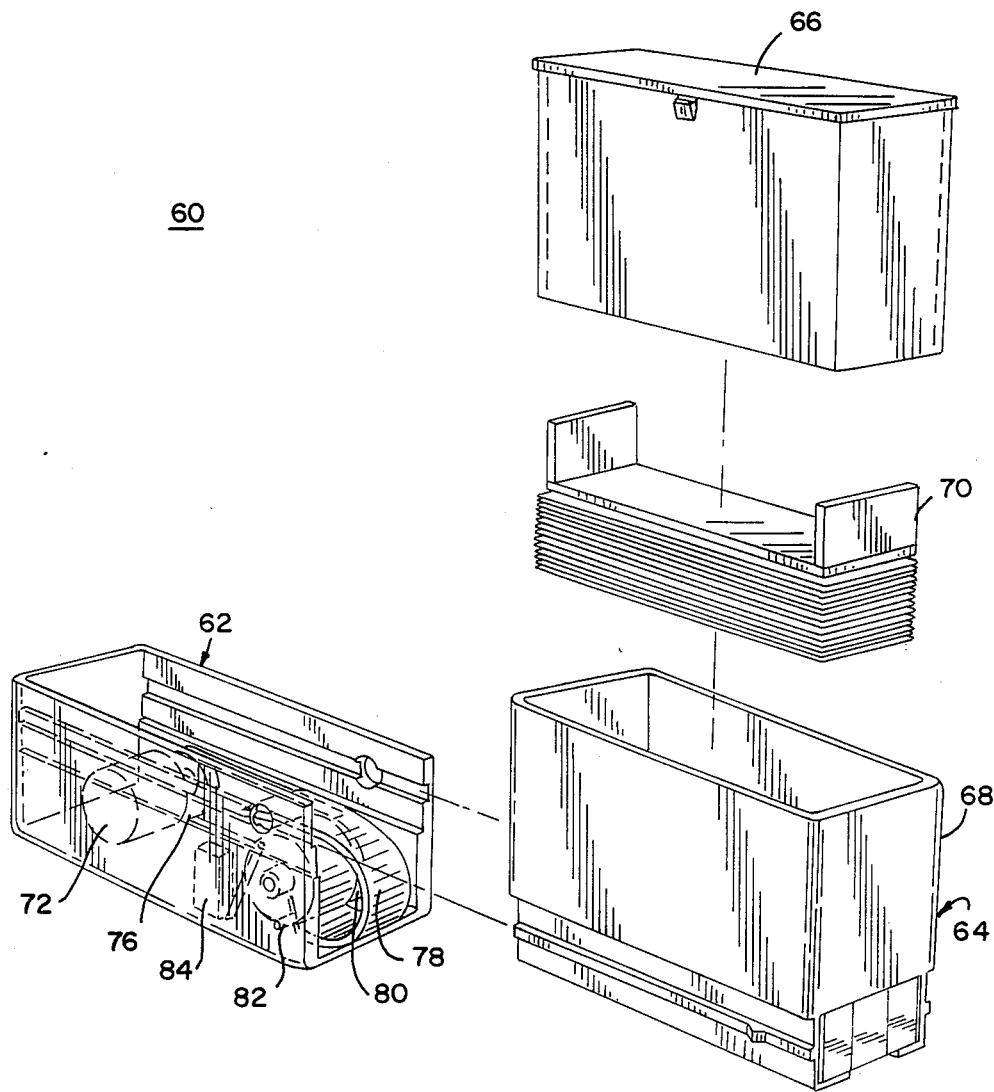

4,872,593

DISPENSER FOR PACKAGED BANDAGES AND THE LIKE

BACKGROUND OF THE INVENTION

This invention relates to dispensers for packaged bandages and the like, and particularly to dispensers of the type of which can be used to dispense single flat packaged units, with power supplied either manually or electrically.

Packaged adhesive bandages are typically sold packed in a metal or cardboard package or canister. Each adhesive bandage is individually wrapped to maintain sterility. To use one of these bandages, the user must open the canister, and either pluck a single bandage therefrom or empty some or all of the contents of the canister, make a selection, and return the remaining bandages to the package.

While the need for efficient dispensing of adhesive bandages may be great in the context of families with small children, it is all the more pronounced in clinical settings. In doctor's offices, emergency rooms and medical laboratories, adhesive bandages are used often, especially to cover the small wounds created when blood is drawn for diagnostic testing.

SUMMARY OF THE INVENTION

The dispenser embodying the present invention provides a simple, efficient and attractive means of dispensing individual packaged adhesive bandages, and may also be used to dispense similarly shaped, elongated, flat product units. The dispenser, in its preferred embodiment, includes a drive unit base and an associated replaceable or refillable product cartridge.

The bandages are stacked in a chamber inside the cartridge and are held in place by a weight or other biasing means. They are stacked on a chamber floor which includes a centrally disposed longitudinally aligned slot. An exit portal is provided at the bottom of one end of the product cartridge in the preferred embodiment. The exit portal is provided with a restraining flap to restrain all but one bandage, to assure that only one bandage at a time is dispensed.

The complete dispenser is assembled by inserting the cartridge into the drive unit base. The drive unit base includes a roller or wheel whose axis is aligned horizontally, perpendicular to the slot defined in the chamber floor, so that a projection or flexible finger attached to the roller can, as the roller is rotated, frictionally engage the lowermost bandage in the cartridge through the slot. In this manner the lowermost bandage is urged against the restraining flap at the end of the slot and propelled out of the exit portal of the dispenser.

In alternative embodiments the roller may be powered manually by a simple crank arrangement or electrically by a motor drive.

The cartridge may be either refillable or replaceable, and may be provided with insertable inner sleeves to accommodate different size bandages.

It is a principal object of the invention to provide a simple, attractive, functional dispenser for packaged adhesive bandages for storage and dispensing of similarly shaped elongated flat product units.

It is another object of the invention to provide such a dispenser for storage and dispensing of similarly shaped elongated flat product units.

It is a further object of the invention to provide such a dispenser for storage and dispensing of individual packaged adhesive bandages which may be either manually or electrically powered.

It is a still further object of the invention to provide such a dispenser which is compact and easily stored.

BRIEF DESCRIPTION OF THE DRAWINGS

FIG. 6 is an exploded view of an alternative embodiment of the dispenser.

DESCRIPTION OF THE PREFERRED AND ALTERNATE EMBODIMENTS

Figure 1:
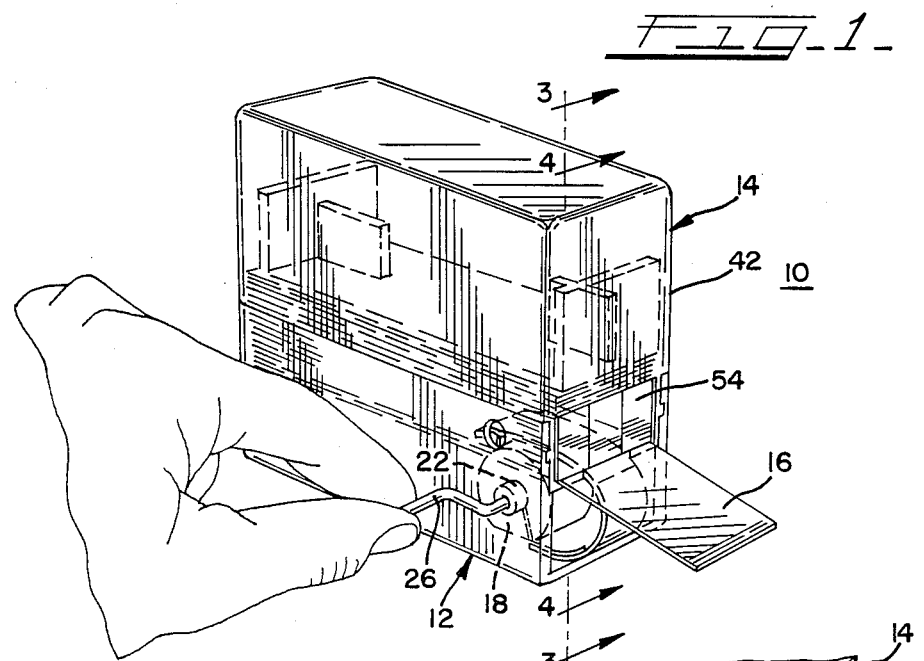
FIG. 1 is a general perspective view of the dispenser embodying the present invention.
Figure 5:
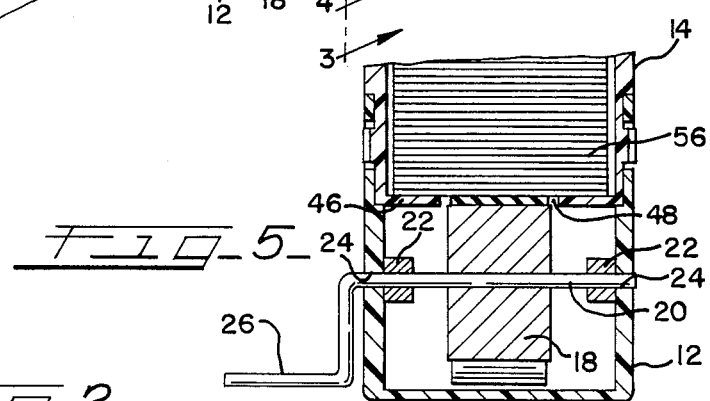
FIG. 5 is a view taken along line 5—5 of FIG. 4.
Figure 2:
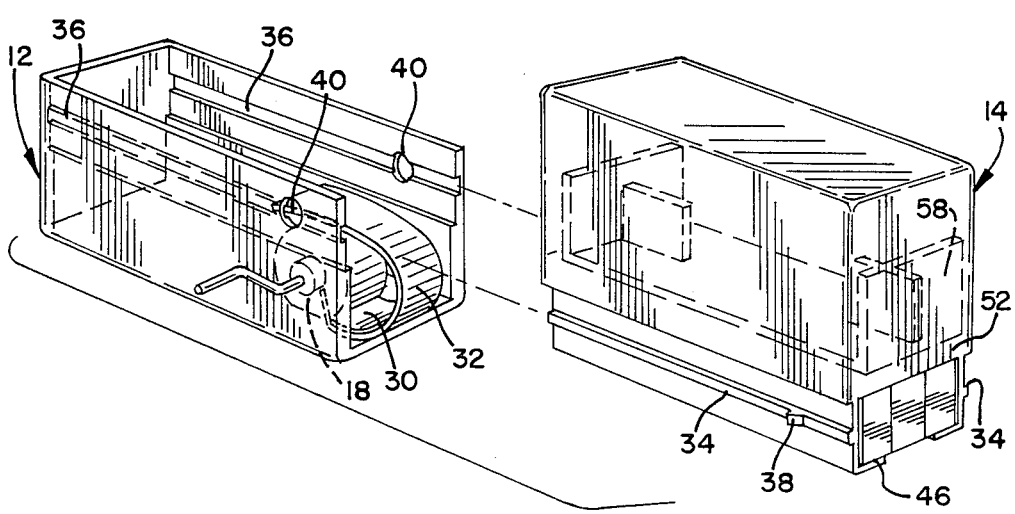
FIG. 2 is an exploded view of the dispenser shown in FIG. 1, with the product cartridge shown disengaged from the base unit.

Referring now to FIG. 1 of the drawings, the bandage dispenser embodying the present invention is generally indicated by reference character 10. In this embodiment the device includes drive unit base 12 connected to product cartridge 14. FIG. 1 is a general perspective view of the preferred embodiment, and shows the dispenser in use dispensing one of the packaged adhesive bandages 16 stored in cartridge 14. Illustrated in phantom within base 12 is roller 18, which is rotatably mounted to base 12 by means of axle 20 which has journals 22 fixed thereto. Bearing sockets 24 are defined in the walls of base 12 to receive axle 20. Roller 18 is fixed to axle 20 and is located substantially midway between the two sides of base 12. Extending from axle 20 through the wall of base 12 is crank 26. The arrangement of these components may be readily appreciated by reference to FIG. 5.

Roller 18 is substantially cylindrical in shape, except that the cylinder is truncated along a plane parallel to the axis of the roller, thereby defining a planar face 28 on roller 18.

Fixed to roller 18 at face 28 is extended anchor 30. As shown in this embodiment anchor 30 is formed out of a resilient, semi-rigid material such as plastic or spring steel. Affixed to anchor 30 is flexible finger 32. Finger 32, as shown in this embodiment, is made of a suitable elastic material, such as natural or synthetic rubber.

Figure 4:
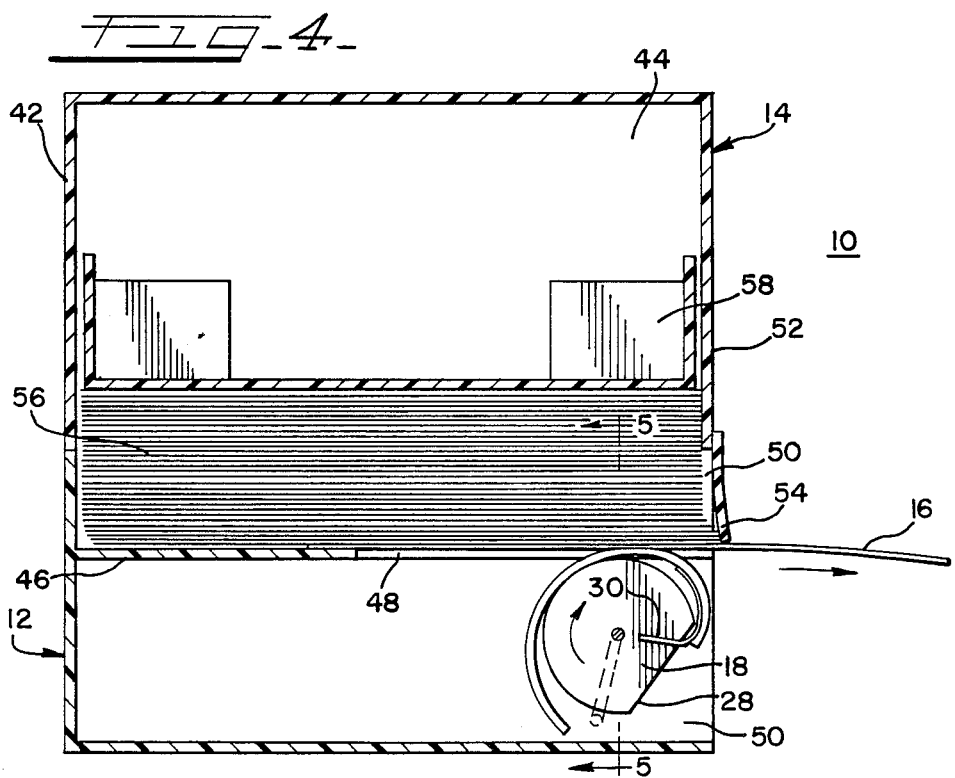
FIG. 4 is a view taken along line 4—4 of FIG. 1 illustrating the operation of the dispenser.

Cartridge 14 slideably engages with drive unit base 12 by slideably mating horizontal tracks 34 on cartridge 14 with respective associated channels 36. To complete the assembly of the unit projecting lugs 38 on tracks 34 engage sockets 40 in channels 36. The truncation of roller 18 provides clearance for the cartridge to slide past roller 18 when face 28 is in the uppermost horizontal position, as shown in FIG. 4.

As illustrated in this embodiment, cartridge 14 includes cartridge housing 42 in which is defined cartridge chamber 44. Cartridge 14 also includes horizontal chamber cartridge chamber floor 46, with elongated slot 48 defined therein. Slot 48 is disposed substantially parallel to the sides of the chamber 44 and located substantially intermediate thereto. Slot 48 extends, in this embodiment, from a point intermediate the ends of chamber 44 to the front end of chamber 44 where the slot is open ended at portal 50 defined in front face 52 of cartridge 14.

Flexible cover flap 54, being of a suitable elastic material, is attached along its top edge to face 52 above portal 50.

Individually packaged adhesive bandages 56 are stacked in cartridge chamber 44 on chamber floor 46 with lowermost bandage 16 resting on floor 46 and exposed to slot 48. Bias weight 58 is disposed within chamber 44, resting on top of stack 56 to maintain the stack in orderly arrangement. It is contemplated that in alternative embodiments other suitable biasing expedients may be used to maintain this arrangement, such as a spring to exert a downward bias against the stack of bandages 56.

Figure 3:
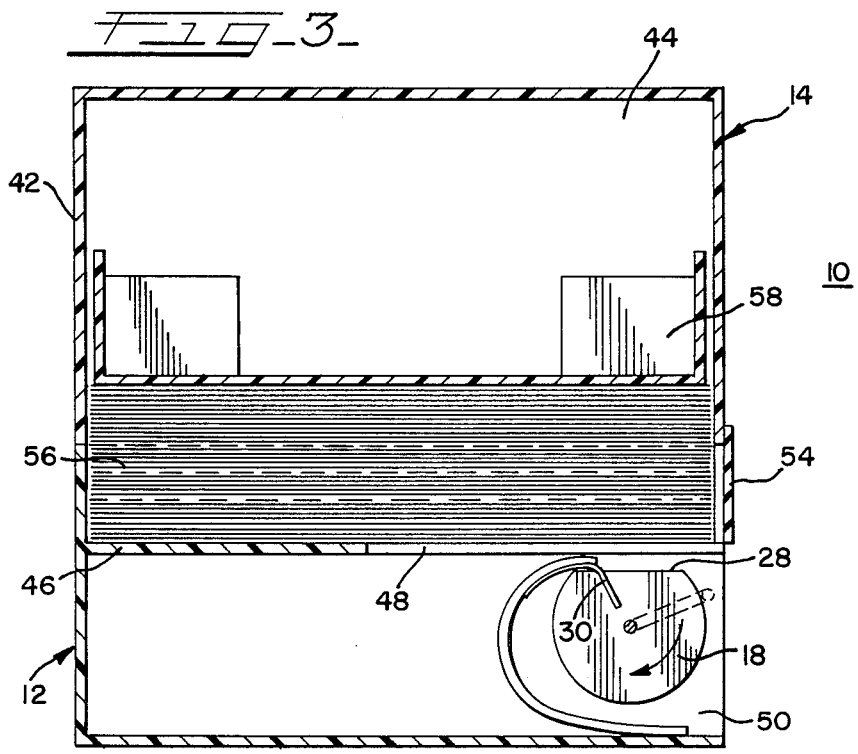
FIG. 3 is a view taken along line 3—3 of FIG. 1 illustrating the operation of the dispenser.

Roller 18, finger anchor 30 and finger 32 are aligned with slot 48 so that when crank 26 is turned in the clockwise direction, finger 32 frictionally engages lowermost bandage 16 through slot 48 as shown in FIGS. 3 and 4. As the roller 18 makes a complete rotation, bandage 16 is urged through portal 50, outwardly displacing cover flap 54, and propelled out of the dispenser as shown in FIG. 4 and in FIG. 1. Elastic cover flap 54 serves to restrain all of the bandages other than the lowermost bandage 16, which is the only one frictionally engaged by finger 32.

Although finger 16 is shown as a flexible, elongated elastic member, it is contemplated that alternative embodiments of this element may be used with similar effect, including a cam, of unitary construction having a projection to frictionally engage lowermost bandage 16 through slot 48.

An alternative embodiment of the present invention is shown in FIG. 6, in exploded view. As shown in this figure, the alternative embodiment of the invention is indicated generally by reference character 60. Dispenser 60 includes motorized drive unit base 62 which is engageable with cartridge 64 in the same manner as in the previously described embodiment. Inner sleeve 66 is slideably fitted into outer sleeve 68 of cartridge 64. Inner sleeve 66 may be variously dimensioned to accommodate various sizes of individually packaged adhesive bandages or similarly shaped product units. Bias weight 70 is provided of suitable dimension to fit within inner sleeve 66, and, as previously discussed, is used to maintain alignment of the stack of bandages within the cartridge chamber by gravity or other suitable bias means.

Drive unit base 62 includes electric motor 72 mounted within base 62. Roller 74 is driven by motor 72 through drive pulley 76, drive belt 78 and driven pulley 80, which is fixed to, and rotatable with, roller 74. Pin 82 is fixed to the side of roller 74 and projects outwardly therefrom, in parallel relation to the axis of roller 74. Switch 84 is mounted to base 72 in opperative proximity to roller 74, and aligned with projecting pin 80.

Electric power to motor 72 is provided through a circuit (not shown) which includes switch 84 in series with motor 72, so that when power is applied to motor 72, roller 74 is driven through one complete revolution, expelling one packaged bandage before switch 84 is tripped by pin 82 to open the electrical circuit, thus interrupting power to the motor.

The foregoing specification describes only the embodiments of the invention shown and/or described. Other embodiments may be articulated as well. The terms and expressions used therefore serve only to describe the invention by example and not to limit the invention. It is expected that others will perceive differences, which, while differing from the foregoing, do not depart from the spirit and scope of the invention herein described and claimed. The invention is to be limited, therefore, only by the scope of the appended claims.

What is claimed is:

1. An apparatus for storage and dispensing of flat package units comprising:
   a base;
   engagement means rotatably mounted within said base;
   said engagement means comprising a substantially cylindrical roller truncated parallel to its axis, said roller having a follower extending from said roller;
   a cartridge slideably mounted to said base, said cartridge defining a chamber therewithin for the storage of flat package units;
   said cartridge having a horizontal track slideably engageable with a horizontal channel in said base and said track having a lug which engages a socket in said channel when said cartridge is in proper horizontal relationship with said base allowing for the proper dispensing of said flat package units;
   said chamber having a floor with a longitudinally disposed elongated slot defined therein alignable with said engagement means;
   means for biasing toward said floor a plurality of flat package units stacked on said floor;
   means associated with said base for rotatably driving said engagement means; and
   an exit portal defined in said cartridge adjacent to one end of said chamber floor,
   whereby rotation of said engagement means causes said engagement means to frictionally engage a lowermost package unit from said plurality in said chamber through said slot only when the cylindrical portion of said roller is in direct contact with the follower and to urge said package unit toward and through said portal.

2. An apparatus as in claim 1 further comprising means associated with said exit portal to substantially restrain the exit of flat package units.

3. An apparatus as in claim 2 wherein said restraining means comprises an resilient flap attached to said cartridge and covering said portal, whereby passage of said lowermost package unit through said exit portal partially displaces said resilient flap.

4. An apparatus as in claim 1 wherein said slot is open-ended and the open end of said slot is substantially co-extensive with said portal.

5. An apparatus as in claim 1 wherein said biasing means comprises an weight positionable on said plurality of packaged units.

6. An apparatus as in claim 1 wherein said follower is attached to a resilient extension anchor attached to said roller.

7. An apparatus as in claim 6 wherein said resilient extension anchor maintains at least a portion of said follower spaced from said roller.

8. An apparatus as in claim 1 wherein said driving means comprises a crank extending from an axle on which said engagement means is mounted.

9. An apparatus as in claim 1 wherein said driving means comprises an electric motor mounted to said base in operative relation with said engagement means.

10. An apparatus as in claim 9 further comprising means operatively associated with said engagement means to interrupt electric power to said electric motor.

11. An apparatus as in claim 10 wherein said interrupting means comprises a pin projecting from said engagement means and a switch in electrical communication with said electric motor and in operative relation with said pin whereby rotation of said engagement means causes said pin to trip said switch, thereby interrupting power to said motor.

* * * * *